United States Patent [19]
Hamamoto et al.

[11] Patent Number: 4,814,278
[45] Date of Patent: Mar. 21, 1989

[54] CULTURE APPARATUS AND METHOD

[75] Inventors: Kimihiko Hamamoto, Hachioji; Michiyuki Tokashiki, Hino; Yataro Ichikawa, Tokorozawa; Takami Arai, Hachioji; Kenji Ishimaru, Iwakuni, all of Japan

[73] Assignee: Teijin Limited, Osaka, Japan

[21] Appl. No.: 55,332

[22] Filed: May 28, 1987

Related U.S. Application Data

[63] Continuation-in-part of Ser. No. 823,632, Jan. 29, 1986, abandoned.

[30] Foreign Application Priority Data

Feb. 5, 1985 [JP] Japan .................. 60-19238
Jun. 10, 1986 [JP] Japan .................. 61-132775
Nov. 12, 1986 [JP] Japan .................. 61-267709

[51] Int. Cl.$^4$ ................................. C12M 3/02
[52] U.S. Cl. ......................... 435/286; 435/315; 435/313
[58] Field of Search ............ 435/286, 314, 313, 316, 435/315

[56] References Cited

U.S. PATENT DOCUMENTS

| | | | |
|---|---|---|---|
| 2,083,348 | 6/1937 | Scholler et al. ................. | 435/314 |
| 3,460,810 | 8/1969 | Mueller ......................... | 435/316 X |
| 3,575,813 | 4/1971 | Rothmayr ...................... | 435/313 X |
| 3,801,468 | 4/1974 | Lumb et al. .................... | 435/315 X |
| 3,963,581 | 6/1976 | Gracobbe et al. ............... | 435/316 X |
| 4,036,699 | 7/1977 | Quigg ............................. | 435/315 X |
| 4,256,837 | 3/1981 | Fluri et al. ..................... | 435/316 |

*Primary Examiner*—Larry Jones
*Attorney, Agent, or Firm*—Wenderoth, Lind & Ponack

[57] ABSTRACT

An apparatus for cell culture by perfusion comprising a cell culture tank for suspension culture, said cell culture tank having a suspension cell culture zone, a cell settling zone, an opening for discharging a spent culture medium from the settling zone and an opening for supplying a culture medium to the suspension culture zone, the suspension culture zone and the setting zone being separated by a partition therebetween in a manner to communicate with each other in the lower portion of the settling zone, and the settling zone being formed between the side wall of the cell culture tank and the partition. Another type of apparatus for cell culture having a unit in which main culturing and settling are carried out in a cell settling zone, and a multiunit cell culture apparatus having at least two culturing units which are stacked longitudinally are also described. A method for culturing cells by perfusion in the culture apparatus which comprises withdrawing a substantially cell-free culture medium from the settling zone and introducing a fresh culture medium into the suspension culture zone.

15 Claims, 6 Drawing Sheets

CULTURE APPARATUS AND METHOD

This is a continuation-in-part application of U.S. patent application Ser. No. 823,632 filed on Jan. 29, 1986 now abandoned.

This invention relates to an apparatus and a method for culturing cells. More specifically, it relates to an apparatus and a method for culturing cells in suspension.

Cell culture technology is important for the production of antiviral agents such as viral vaccines and interferons of biochemicals such as hormones. The recent production of monoclonal antibodies having the ability to bind to a particular protein as a target relies on the culture of a hybridoma obtained by fusing antibody-producing cells with myeloma cells, and the solution of problems associated with this technique is an industrially important subject.

Heretofore, cell culture has been carried out on a laboratory scale by using a Petri dish, a test tube, a culture bottle, etc.

Some methods and apparatuses for cell culture have recently been suggested. They are roughly classified into anchorage-dependent culture systems and suspension culture systems selected according to the properties of a particular cell to be cultured.

A suspension cell culture method was proposed in which a spinner flask is given stirring function by a magnetic stirrer of by a vane wheel on a mechanically driven shaft (see U.S. Pat. Nos. 2,948,517 and 3,649,465).

Japanese Laid-Open Patent Publication No. 65180/1982 proposed a suspension culture apparatus in which at least one flexible sheet of a relatively large area supported on a rotatable shaft is used as a stirrer and the desired gentle stirring is created for a certain kind of feeble cells such as human diploid cells by rotating the stirrer sheet and thus causing it to undulate. In cell culture by this apparatus, the cells are cultured in a fixed amount of nutrients, and the growth of the cells stops while they are at a relatively low cell density.

To prevent the growth of cells from stopping at a relatively low cell density and to culture the cells in large quantities at a high density in suspension, there was proposed a so-called perfusion method comprising culturing cells while supplying a makeup culture medium to a culture tank and in the meantime, discharging the spent medium containing a growth-inhibitor substance out of the tank. In performing culture by this method, it is important to separate the spent medium efficiently from living cells in the suspension and discharge the spent medium out of the tank, and thereby to maintain the growth environment for the cells in the tank under optimum conditions. Various filters or other systems have been proposed for the separation of living cells and the spent medium from the suspension. None of them, however, have proved to be entirely satisfactory for industrial pratice because of one or more disadvantages such as the blockage of the filters of the complexity of the structure of the systems.

Japanese Laid-Open Patent Publications Nos. 82083/1984 and 9482/1985 proposed an apparatus for culturing suspended cells at a high density which comprises a culture supernatant discharging tube concurrently functioning as a cell settling tube and a line for addition of a fresh medium so that the cell culture is effected while adding the fresh medium from the line and simultaneously discharging the culture supernatant from the discharge tube.

Generally, suspended animal cells are as small as several microns to about ten microns in size, and their specific gravity is not much different from that of the culture medium. Hence, in the aforesaid apparatus adapted for separating the suspended cells from the spent medium, the settling area should be increased to settle the cells advantageously. In the apparatuses disclosed in the above two Japanese patent documents, however, the settling area cannot be made so large as is desired.

It is an object of this invention therefore to provide an apparatus of a simple structure which enables living cells and the spent medium to be separated from a cell suspension, and a method for cell culture in suspension using the apparatus.

Another object of this invention is to provide an apparatus and a method which enable living cells to be separated from the spent culture medium without using a filter or the like, and therefore, offer a solution to the problems associated with filter blockage, etc.

Still another object of this invention is to provide an apparatus and a method for carrying out a suspension cell culture in an industrially advantageous way in which the settling area for the advantageous achievement of cell settling can be increased very much.

Yet another object of this invention is to provide an apparatus and a method in which dead cells and their debts that frequently become a problem in suspension cell culture in general can be removed easily out of a culture tank.

A further object of this invention is to provide an industrial apparatus and an industrial method which are suitable for the culture of cells in large quantities at a high density by the perfusion technique.

Additional objects and advantages of this invention will become apparent from the following description.

According to this invention, the above objects and advantages of this invention are first achieved by an apparatus for cell culture by perfusion comprising a cell culture tank for suspension culture, said cell culture tank having a suspension cell culture zone, a cell settling zone, an opening for discharging a spent culture medium from the settling zone and an opening for supplying a fresh culture medium to the suspension culture zone, the suspension culture zone and the settling zone being separated by a partition therebetween in a manner to communicate with each other in the lower portion of the settling zone, and the settling zone being formed between the side wall of the cell culture tank and the partition.

According to this invention, living cells sediment downwardly in the direction of gravity in the settling zone, and the spent culture medium and the cell debris are separated in the upper portion of the settling zone. Hence, the spent culture medium which is substantially free of living cells can be discharged from the discharge opening provided in the upper portion of the settling zone. Consequently, the present invention enables living cells to be separated efficiently from the spent medium by a simple method without using a filter, and therefore can be applied to the culture of large amounts of cells at a high density.

The culture apparatus of this invention includes a suspension cell culture zone which can be defined as a zone wherein cells can be substantially cultured in the suspended state and a cell settling zone which can be defined as a zone wherein the grown cells are separated from the spent culture medium by gravity. The suspension cell culture zone and the cell settling zone are separated by a partititon so that they communicate with each other in the lower portion of the settling zone within the cell culture tank. Because of this structure, the cells which have settled in the cell settling zone and have been separated from the spent medium are again introduced into the suspension cell culture zone via the lower portion of the settling zone and cultured again in the culture zone.

The settling zone within the culture tank is formed between the side wall of the culture tank and the partition. This structure has the advantage of greatly increasing the effective settling area of the settling zone in the culture tank.

The culture tank of the apparatus of this invention also has an opening for discharging the spent medium separated from the cells in the settling zone and an opening for supplying a makeup culture medium to the culture zone.

In the culture tank of the apparatus of this invention, the settling zone is formed between the side wall of the culture tank and the partition preferably in a manner to surround the suspension cell culture zone. In this preferred embodiment, the suspension cell culture zone and the settling zone are separated by, for example, a cylindrical partition. In this case, it is further preferred that a substantial portion of the tank side wall facing the cylindrical partition is cylindrical and the cylindrical partition and the cylindrical side wall are located substantially concentrically.

The apparatus of this invention may further include means for facilitating the settling of the cells provided in the settling zone. Such means is adapted to shorten the distance in the direction of gravity over which the cells settle, and may, for example, be a settling plate provided within the settling zone in a direction across the direction of gravity, as shown FIG. 7.

A baffle plate extending in the direction of gravity and partitioning the settling zone may be provided in the settling zone to minimize the mixing effects by the flowing of the culture medium in the suspension cell culture zone. It will be easily understood that the baffle plate, if provided in the settling zone angularly to the direction of gravity, exhibits the function of the settling plate.

The culture tank of the apparatus of this invention may be equipped with means for forcibly stirring the culture medium in the suspension cell culture zone. Such means may, for example, be mechanical stirring means for suspending the cells forcibly in the culture medium. It is also possible to provide an oxygen-containing gas introduction opening, alone or in combination with an oxygen-containing gas guiding cylinder, in the culture tank, and to suspend the cells forcibly in the culture medium under the effect of stirring created by the upward movement of the oxygen-containing gas introduced from the introduction opening.

The cell culture apparatus of this invention is applicable to suspension cell culture. The suspension culture denotes the growing of cells suspended in an aqueous medium or suspended therein while carried on microcarriers, or the growing of cells in microcapsules. In particular, the present invention can be advantageously used for culturing the cells suspended freely.

The cells that can be cultured in the cell culture apparatus of this invention may include plant cells, animal cells and microorganism cells. They may also be cells modified artificially or by gene manipulation, for example hybridoma cells. The apparatus of this invention is particularly suitable for culturing animal cells.

In the suspension cell culture tank in the present invention, cells to be grown are cultured suspended in the culture medium. The culture medium is composed of an aqueous medium consisting substantially of water and various additives used generally in cell culture, such as inorganic salts, vitamins, coenzymes, glucose, amino acids and antibiotics. Serum may be added to the culture medium, and a so-called serum-free culture medium may also be used.

The method of this invention to culture cells by perfusion can be advantageously carried out by withdrawing a substantially cell-free spent medium from the settling zone and introducing a makeup culture medium into the suspension cell culture zone.

At this time, the ratio of the volume (V, cm$^3$) of the culture medium within the suspension cell culture zone to the effective settling zone (S, cm$^2$), V/S, is within the range of preferably 0.1 to 500 cm, especially preferably 1 to 100 cm.

The apparatus and method of this inventin will now be described in greater detail with reference to the accompanying drawings, in which.

Figure 1:
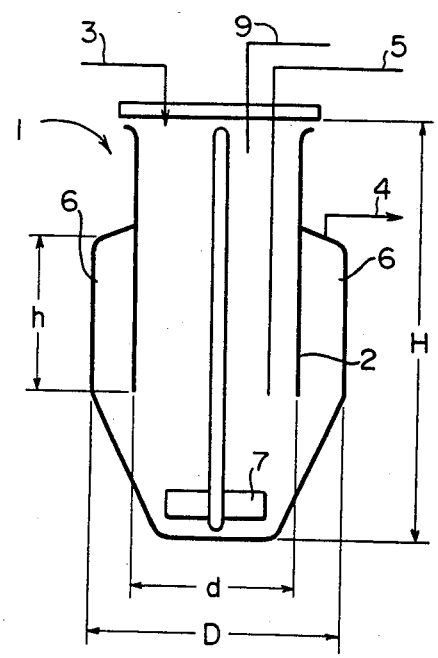
FIGS. 1 and 2 are simplified views generally showing the apparatus of this invention.

With reference to FIG. 1, a settling zone 6 defined by a partition wall 2 is provided inwardly of the wall of a culture tank 1. The culture tank 1 has a culture medium supply opening leading to a line 3 for supplying a fresh culture medium. Oxygen or a gas containing oxygen is introduced into the culture tank through a line 5, and a line 9 is also provided for discharging the waste gas. In the upper portion of the settling zone is provided an opening for discharging the spent culture medium out of the culture tank through a line 4.

A stirrer 7 is provided in the culture tank 1. By rotating it, the cells are maintained in the suspended state.

Figure 2:
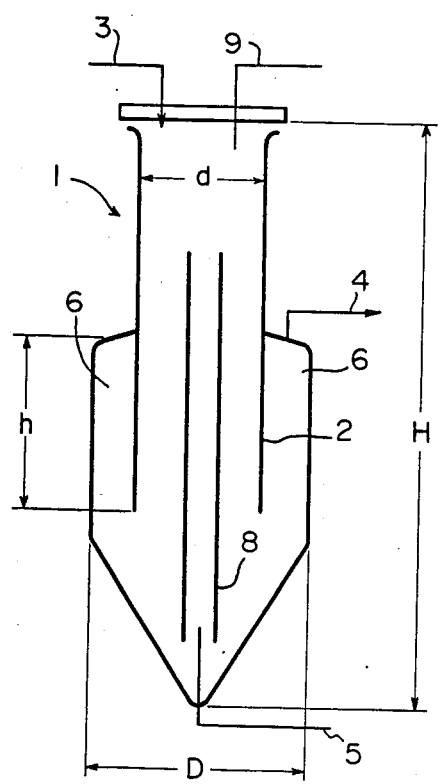

In FIG. 2, the reference numerals 1 to 6 mean the same parts 1 to 6 in FIG. 1 having the same functions. The difference of the apparatus shown in FIG. 2 from that shown in FIG. 1 is that a guide cylinder 8 is provided in the culture tank 1, and oxygen or a gas containing oxygen is supplied to the lower portion of the guide cylinder 8 via a line 5. By feeding oxygen or the oxygen-containing gas into the lower portion of the guide cylinder 8, the suspension rises within the guide cylinder 8 from bottom to top, while the downward movement of the suspension takes lace exteriorly of the guide cylinder 8. Consequently, the suspension as a whole is stirred.

In both FIGS. 1 and 2, the stirring effect of the suspension is not substantially exerted on the settling zone 6 defined by the partition wall 2 inwardly of the wall of the culture tank 1. The settling zone 6 is designed such that within it, the cells settle in the direction of gravity and the spent culture medium which is substantially free from the cells and contains a growth-inhibiting substance remains in the upper portion of the settling zone.

Advantageously, as shown in FIGS. 1 and 2, the culture tank has a height (H)/diameter (D) ratio, H/D, of from 0.5 to 10, preferably from 1 to 5. The shape of the tank as a whole may be chosen from various shapes generally used in suspension cell culture.

The settling zone is not limited in shape and structure so long as it provides a space in which the linear velocity of the culture medium is slower than the settling velocity of the cells and to which the stirring of the suspension within the culture tank does not extend.

In the apparatuses shown in FIGS. 1 and 2, the settling zone 6 is separated from the suspension culture zone by the partition wall 2 in cylindrical form, and a substantial portion of the tank side wall facing the cylindrical partition wall 2 is cylindrical. The cylindrical partition wall 2 and the cylindrical tank side wall are positioned substantially concentrically.

In these apparatuses, S as a basis for calculating V/S (where V is the volume of the culture medium in the suspension culture zone and S is the effective cell settling area) is expressed by the following equation.

$$S = \frac{\pi}{4}(D^2 - d^2)$$

where D is the diameter of the cylindrical portion of the side wall of the tank, and d is the diameter of the cylindrical partition wall 2.

It should be understood that V is the volume obtained by subtracting the volume of an empty space where no culture medium exists and the volume of the settling zone from the volume of the culture tank.

Figure 3:
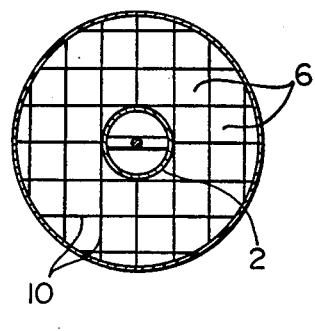
FIG. 3 is a top plan view of one embodiment of the apparatus of this invention.
Figure 4:
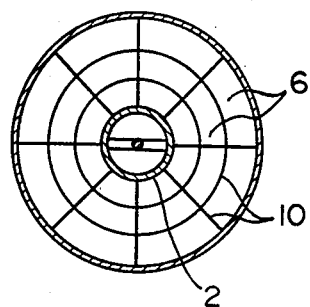
FIG. 4 is a top plan view of another embodiment of the apparatus of this invention.
Figure 5:
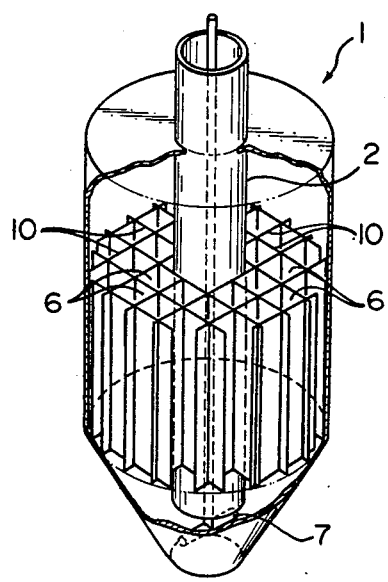
FIG. 5 is a vertical sectional view of the apparatus shown in FIG. 3.
Figure 6:
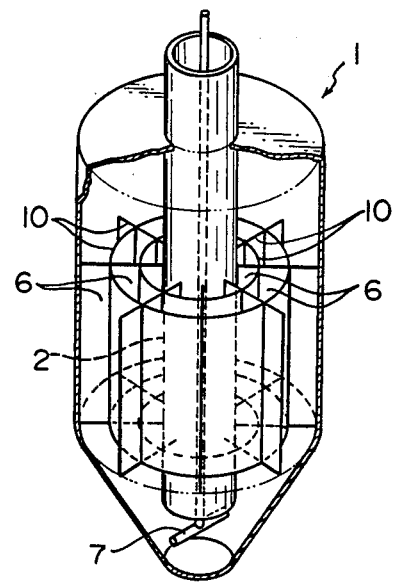
FIG. 6 is a vertical sectional view of the apparatus shown in FIG. 4.

With reference to FIGS. 3 and 4, a baffle plate 10 is provided in the settling zone 6. The baffle plate 10 may be arranged such that the divided settling zone forms a lattice-like pattern as shown in FIG. 3, or a fan-like pattern as shown in FIG. 4. The vertical sections of the apparatuses shown in FIGS. 3 and 4 are shown respectively in FIGS. 5 and 6 in a simplified manner.

Figure 7:
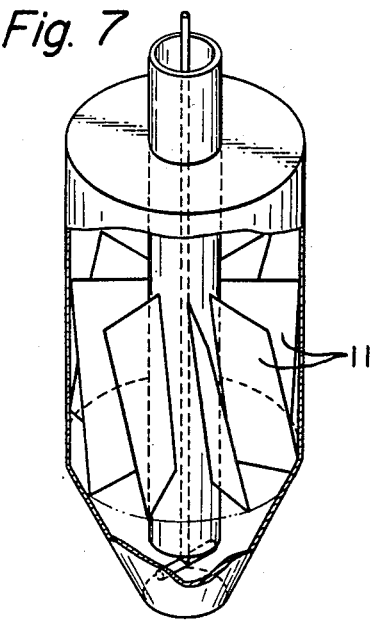
FIG. 7 is a simplified vertical sectional view of still another embodiment of this invention.

In the apparatus shown in FIG. 7, settling plates 11 are provided in the settling zone.

Figure 8:
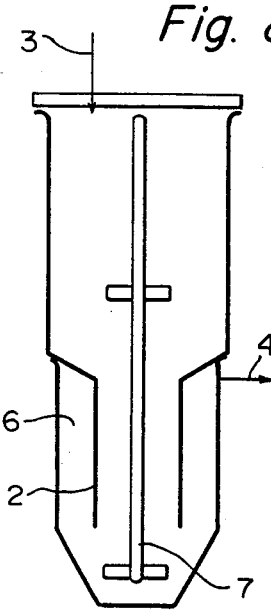
FIG. 8 is a simplified vertical sectional view of yet another embodiment of the apparatus of this invention.

In the apparatus shown in FIG. 8, the settling zone 6 extends halfway in the direction of the height of the culture tank, and the apparatus is constructed as if the suspension culture zone were formed in two stages. A stirrer is also provided in the upper stage of the suspension culture zone.

Generally, devices for measuring the concentrations of oxygen, carbon dioxide, and nutrients or the pH of the culture medium are provided in culture apparatuses. Needless to say, the cell culture tank of this invention is also equipped with such devices.

In carrying out the method of this invention, the fresh culture medium used is an aqueous solution of nutrients such as glucose and proteins and components required for cell culture such as various amino acids, inorganic salts and antibiotics, which may, or may not, contain serum.

The culture medium is supplied to the suspension culture zone from the culture medium supply opening, for example one provided at the top of the culture tank as shown in FIGS. 1 and 2. Alternatively, it may be directly supplied to the suspension in the tank through a supply line.

Desirably, in the practice of the method of this invention, the makeup culture medium is supplied, and the spent medium is discharged, so as to maintain a nearly fixed liquid level in the culture tank, although this is not essential. Supplying of the makeup culture medium and discharging of the spent medium may be carried out independently from each other either continuously or intermittently.

In the method of this invention, the oxygen concentration of the suspension is maintained constant by supplying oxygen or a gas containing oxygen directly to the suspension, or by other supplying means. An example of the other supplying means is to use an oxygen carrier. The oxygen carrier may be a liquid compound substantially immiscible with water and being capable of dissolving oxygen. Examples are various fluorocarbons used as a material for artificial blood. In using the fluorocarbons as means for supplying oxygen, a fluorocarbon having oxygen dissolved in it is added in liquid droplets or as a thin film to the suspension from above.

Figure 9:
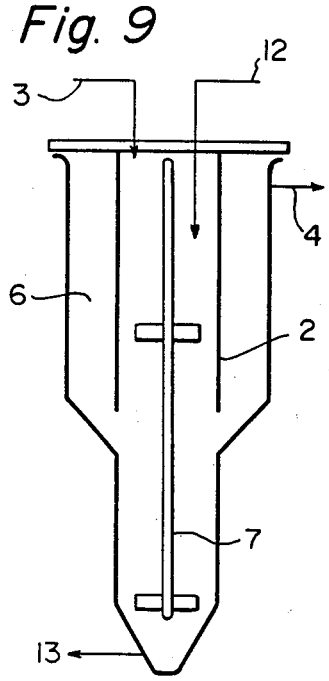
FIG. 9 is a simplified vertical sectional view of a further embodiment of the apparatus of this invention which has means for introducing oxygen into a culture tank using a fluorocarbon as an oxygen-carrier.

In the apparatus of FIG. 9, the suspension culture zone extends further downwardly as compared with the apparatus shown in FIG. 1. A fluorocarbon having oxygen dissolved in it is introduced into the suspension culture zone from a fluorocarbon introduction opening 12, and during its downward movement, makes contact with the culture medium to supply oxygen to it. Thereafter, the fluorocarbon gathers at the bottom of the culture tank, and is withdrawn from a fluorocarbon discharge opening 13.

To perform cell culture efficiently by using the culture tank is accordance with the invention, it is necessary to supply a makeup culture medium and oxygen uniformly to the suspension in the culture tank and meanwhile discharge the spent medium out of the tank. For this purpose, the suspension is desirably in the well stirred state. The stirring may be carried out, for example, by a mechanical stirring method by the rotation of a stirrer vane as shown in FIG. 1, a method relying on a draft effect using a guide cylinder as shown in FIG. 2, or a method which performs oxygen supply and stirring simultaneously by using an oxygen carrier having oxygen dissolved therein as stated above. Two or more such stirring means may be used in combination, as required.

The ratio of the amount of the makeup culture medium to be supplied per day to the effective culture volume (V) of the culture tank (the amount of the makeup culture medium supplied/V) is suitably from 0.2 to 10, preferably from 0.5 to 5.

Thus, according to this invention, the spent medium free from living cells can be easily separated in the suspension culture of cells. The cell debris can also be removed from the suspension together with the spent medium. The apparatus of this invention is simple in structure and is not complex in operation. Hence, it can be suitably used in industrial practice and can be advantageously used for the culture of large quantities of cells at a high density.

According to this invention, the above objects are further achieved by a multiunit cell culture apparatus for cell suspension, comprising at least two culturing units and an opening for supplying a culture medium, each of said units comprising a culture zone for suspension culture of cells, a cell settling zone and a discharge opening for the culture medium from the top of the settling zone, said suspension culture zone and said settling zone being separated from each other by a partition so that they communicate with each other through the bottom part of the settling zone, said settling zone being formed between the outside wall of the culturing unit and the partition, and the culturing units being stacked longitudinally so as to permit flowing of the culture medium.

The multiunit culture apparatus of this invention is roughly understood as having a structure such that a plurality of the above culture apparatuses each constituting a culturing unit are stacked.

The multiunit culture apparatus of this invention has at least two, preferably 2 to 10, more preferably 2 to 5, culturing units.

The multiunit culture apparatus of this invention has at least one discharge opening for discharging the spent culture medium separated from cells in the settling zone of each culturing unit and at least one opening for supplying a fresh culture medium to the culture apparatus at any desired places of the apparatus. Desirably, the supply opening is provided in the upper part of the apparatus.

Perfusion culture of cells in the multiunit culture apparatus of this invention is advantageously carried out by withdrawing the culture medium substantially free from cells from the settling zone and introducing a fresh culture medium into the culture apparatus. At this time, the ratio of the volume (V, cm$^3$) of the culture medium in the suspension culture zone to the effective settling area (S, cm$^2$) of cells, V/S, is preferably 0.1 to 500 cm, especially preferably 1 to 100 cm.

It should be understood that the foregoing description is applicable, in principle, to a description of the multiunit culture apparatus of this invention.

The multiunit cell culture apparatus of this invention will be described in detail with reference to FIGS. 11 to 13.

Figure 11:
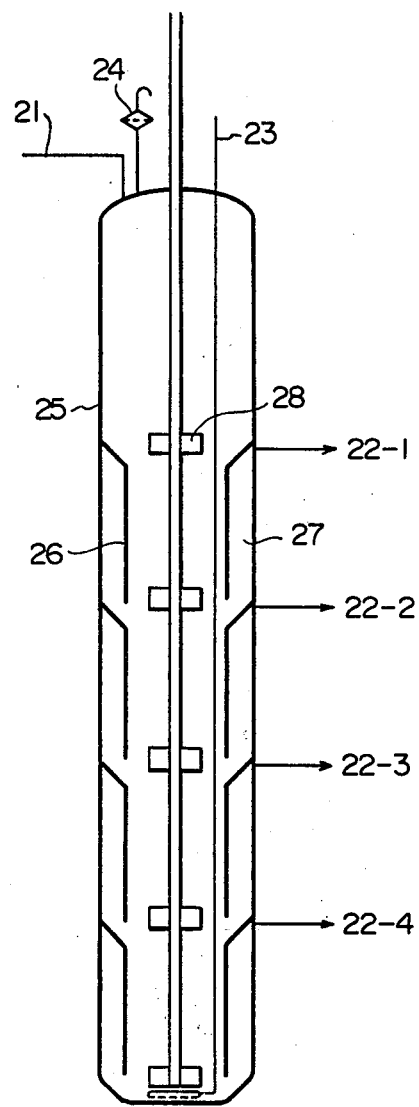
FIGS. 11 to 13 are simplified vertical sectional views of the multiunit culture apparatus in accordance with this invention.
Figure 12:
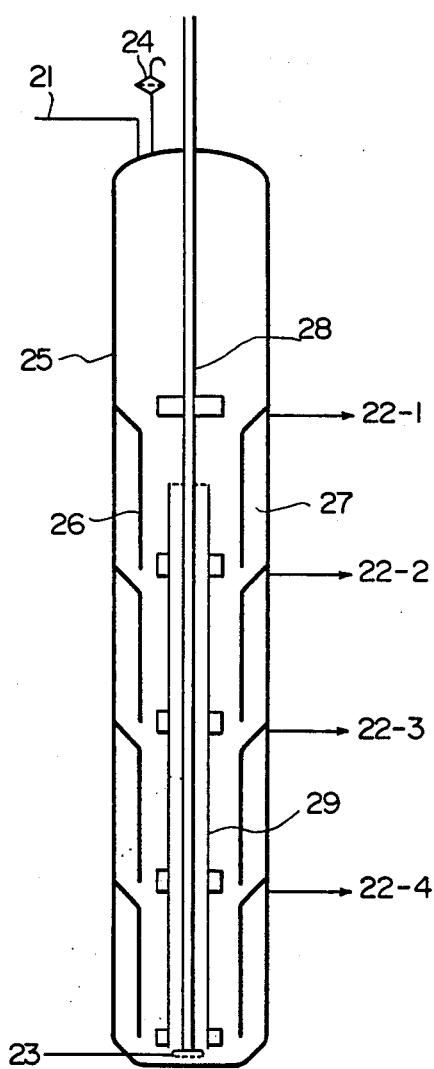
Figure 13:
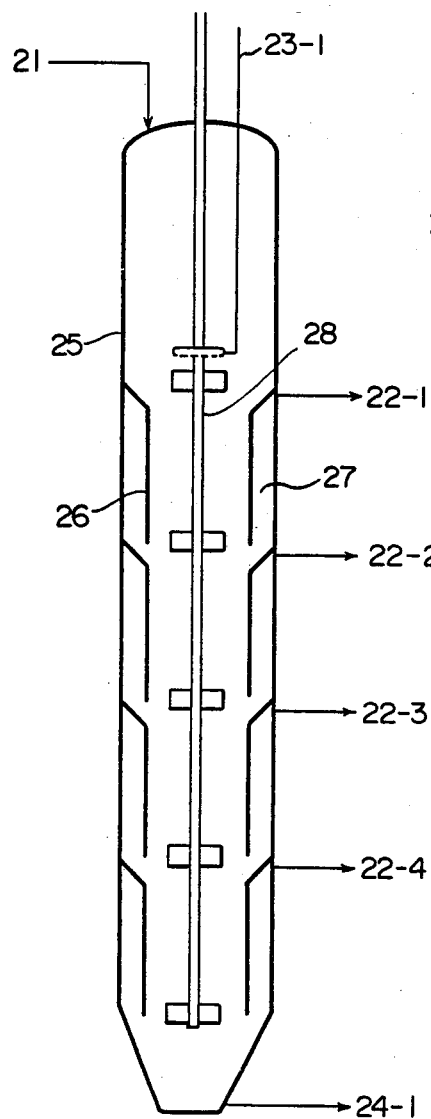

With reference to FIGS. 11 to 13, a settling zone 27 partitioned by a partition wall 26 is provided inwardly of the inner wall of a main body 25 of the culture apparatus. The culture apparatus 25 is equipped with a supply opening for supplying a fresh culture medium via a supply line 21, and molecular oxygen or a molecular gas-containing gas is supplied via a line 23. A discharge line 24 for discharging the waste gas is provided. A discharge opening for the spent culture medium is provided in the upper part of the settling zone 27 so as to discharge the spent culture medium out of the culture apparatus via lines 22-1 to 22-4.

In the multiunit culture apparatus of this invention, one culturing unit may be defined as a zone ranging from the discharge opening 22-1 to 22-2 in a section of the apparatus taken at right angles to the longitudinal direction of the apparatus.

In FIG. 11, a stirring device 28 is provided in the culture apparatus, and by rotating it, cells are maintained in suspension.

In FIG. 12, the reference numerals 21 to 28 have the same meanings as in FIG. 11. The difference from FIG. 11 is that a guide cylinder 29 is provided in the culture tank 27, and molecular oxygen or a molecular oxygen-containing gas is supplied to the lower part of the guide cylinder 29 through line 23. By supplying molecular oxygen or a gas containing molecular oxygen to the lower part of the guide cylinder 28, the suspension rises from bottom to top within the guide cylinder and exteriorly of the guide cylinder 29, the suspension moves conversely from top to bottom. As a result, the suspension is stirred as a whole.

FIG. 13 shows an outline view in vertical section of a device for introducing oxygen dissolved in a fluorocarbon into the culture tank. In the apparatus shown in FIG. 13, a fluorocarbon having oxygen dissolved therein is introduced from a fluorocarbon introducing inlet 23-1, and during its downward movement, makes contact with the culture medium and supplies oxygen to it. Thereafter, it gathers at the bottom portion of the culture tank and is discharged from a fluorocarbon discharge opening 24-1. Except for reference numerals 23-1 and 24-1, reference numerals 21 to 28 in FIG. 13 mean the same members as in FIG. 11.

In FIGS. 11 to 13, a settling zone 27 defined by a partitioning wall 26 is provided inwardly of the inside wall of the culture apparatus, and the stirring effect of the suspension does not substantially extend to the settling zone. The inside of the settling zone 27 is so designed that cells settle in the direction of gravity and the spent culture medium containing growth-inhibiting substances and being substantially free from the cells exists in the upper part.

The settling zone is not restricted in shape and structure, and may be a zone in which the linear speed of the culture medium in it is lower than the settling speed of the cells and to which the stirring of the suspension in the culture tank does not extend.

In the apparatuses of FIGS. 11 to 13, the settling zone 27 is separated from the suspension culture zone by the cylindrical partitioning wall 26. The substantial portion of the side wall of the tank facing the cylindrical partitioning wall 26 is cylindrical, and the cylindrical partitioning wall and the cylindrical tank side wall are positioned substantially concentrically.

A fresh culture medium is supplied to the suspension culture apparatus from the culture medium supply opening provided, for example, in the upper part of the culture apparatus as shown in FIGS. 11 to 13. Alternatively, it may be supplied to the suspension directly through a conduit.

In practicing the cell culture method using the apparatus of this invention, the supply of the fresh culture medium and the discharge of the spent culture medium may desirably be performed such that the liquid level of the culture apparatus is maintained nearly constant.

The supply of the fresh culture medium and the discharge of the spent culture medium, independently from each other, may be performed continuously or intermittently.

According to this invention, the objects of this invention are also achieved by a cell culture apparatus for perfusion culture comprising a cell culture tank for suspension culture, said cell culture tank having a molecular oxygen supply zone, a cell settling zone, a discharge opening for discharging the culture medium from the settling zone and a culture medium supply opening, the molecular oxygen supply zone and the settling zone being separated from ech other by a partition so as to communicate with each other through the bottom of the settling zone, the settling zone being formed between the partition and the side wall of the cell culture tank, and the main culturing and settling of cells being carried out in the cell settling zone.

The above culture apparatus has such a structure that the main culturing and settling of cells are carried out in the settling zone. Hence, this embodiment of the apparatus of this invention has a molecular oxygen supply zone which may be said to be a zone whose main function is to receive a supply of molecular oxygen rather than the culture zone in which main culturing is carried out in the aforesaid apparatus of this invention.

In a cross section of this culture apparatus taken at right angles to the gravity direction of the apparatus, the area of the settling zone is, for example, at least equal to that of the molecular oxygen supply zone. The outside diameter of the settling zone is preferably at least 10 cm. The culturing of cells using the above apparatus in order to perform stirring for main culturing and effective settling of cells can, therefore, be carried out by forming at the bottom of the culture tank of the above culture apparatus a layer of a liquid medium which (a) is not substantially miscible with water, (b) has a higher density than water, and (c) does not substantially inhibit the growth of animal cells, culturing the animal cells while stirring the layer of the liquid medium and transmitting the effect of this stirring to the culture medium located on the liquid medium, withdrawing the culture medium substantially free from the cells from the settling zone, and introducing a fresh culture medium into the culture tank.

A perfluorocarbon, for example, is conveniently used as the liquid medium.

Advantageously, the perfluorocarbon is liquid at ordinary temperature, and commercially available grades can be widely used. For example, fluorocarbons used as various heat media and electrical insulating materials and fluorocarbons used as artificial blood may be used. Specific examples include perfluoroalkanes having at least 8 carbon atoms, perfluorocycloalkanes (such as perfluorodecalin, perfluoromethyldecalin and perfluoroalkylcyclohexanes having a $C_3$–$C_5$ alkyl substituent), perfluoroalkyltetrahydrofurans having a $C_5$–$C_7$ alkyl substitutent, perfluoroalkyltetrahydropyrans having a $C_4$–$C_6$ alkyl substituent, and perfluoroadamantanes (such as perfluoroadamantane, perfluoromethyladamantane, perfluorodimethyladamantane, perfluorodimethylethyladamantane and perfluorodiethyladamantane). The above fluorocarbons may contain various groups such as a tertiary amino group.

The above culture tank and the method of culture will be described with reference to FIG. 14 which shows an outline view of the culture apparatus in the above embodiment.

Figure 14:
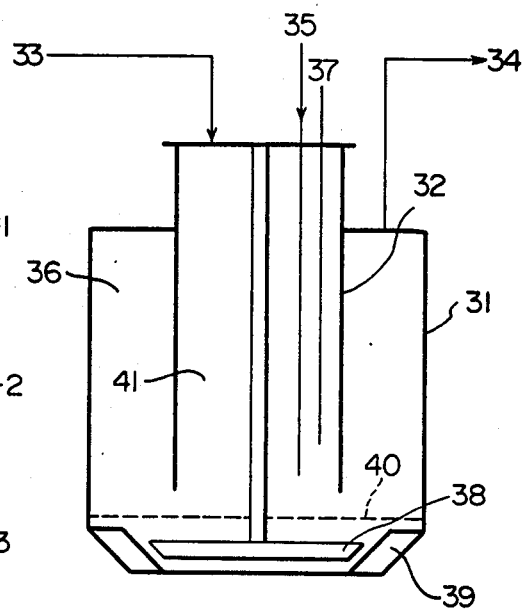
FIG. 14 is a simplified vertical sectional view of the culture apparatus of this invention for performing main culturing and settling of cells in a cell settling zone.

In FIG. 14, a settling zone 36 defined by a partition wall 32 is provided inwardly of the inside wall of a culture tank 31. The culture tank 31 has a supply opening for supplying a frech culture medium through a supply line 33, and molecular oxygen or a molecular oxygen-containing gas is supplied to the culture tank 31 via a line 35. An oxygen concentration detecting sensor 37 is attached to the culture tank 31. A discharge line for waste gases (not shown) is also provided. A discharge opening for the spent culture medium is provided in the upper part of the settling zone 36 so as to discharge the spent medium out of the tank via a line 34. A baffle plate 39 is installed at the bottom of the culture tank 31.

A liquid medium is introduced into the bottom of the culture tank 31 to form a liquid medium layer 40. The dotted line in FIG. 14 represents the interface between the liquid medium layer and the culture medium. Advantageously, the thickness of the liquid medium layer is such that its top (the position at dotted line 40) is away from the bottom part of the partition 32, namely it does not reach the bottom part of the partition 32.

A stirring impeller 38 is provided in the liquid medium layer, and the baffle plate 39 is also positioned in the liquid medium layer.

When the liquid medium layer 40 is stirred by the stirring impeller 38, the liquid medium is stirred but the rotation of the stirring impeller is hampered by the baffle plate 39 and the surface of the liquid medium undulates. The undulation of the surface of the liquid medium layer is transmitted to the culture medium located above it and the cells in it are maintained in suspension.

In the culture tank, the settling zone 36 and a molecular oxygen supply zone 41 are separated from each other by the cylindrical partition wall. The substantial portion of the side wall of the tank which faces the cylindrical partitioning wall is cylindrical, and the cylindrical partition wall and the cylindrical side wall of the tank are positioned substantially concentrically.

The above apparatus can have an increased culturing efficiency by constructing it from a multiplicity of culturing units.

This multiunit culture apparatus is a cell culture apparatus for suspension culture comprising at least two culturing units and an opening for supply of a culture medium, each of the units comprising a cell flowing zone, a cell settling zone and a discharge opening for discharge of the culture medium from the top of the settling zone, the cell flowing zone and the cell settling zone in each said unit being separated from each other by a partition so as to communicate with each other through the bottom site of the settling zone, said settling zone being formed between the outside wall of the culturing unit and the partition, the culturing units being stacked longitudinally so as to permit flowing of the culture medium through the flowing zone, the main culturing and settling in each unit being carried out in the cell settling zone.

As in the case of the multiunit culture apparatus described hereinabove, this multiunit culturing apparatus has at least two, preferably 2 to 10, more preferably 2 to 5, culturing units stacked longitudinally.

Each unit of this multiunit apparatus has a settling zone in which the main culturing and settling of cells are carried out, and therefore has the flowing zone whose main function is to permit flowing of the culture medium between the culturing units rather than to supply molecular oxygen. Supplying themolecular oxygen to this multiunit apparatus can be carried out, for example, only in the flowing zone of the lowermost unit of the stack of units. Alternatively, it may be carried out in two or more flowing zones of the apparatus.

It should be understood that the foregoing description is applied in principle to a description of each of the culturing units of this multiunit culture apparatus.

This multiunit culturing apparatus will be described in detail with reference to FIG. 15.

Figure 15:
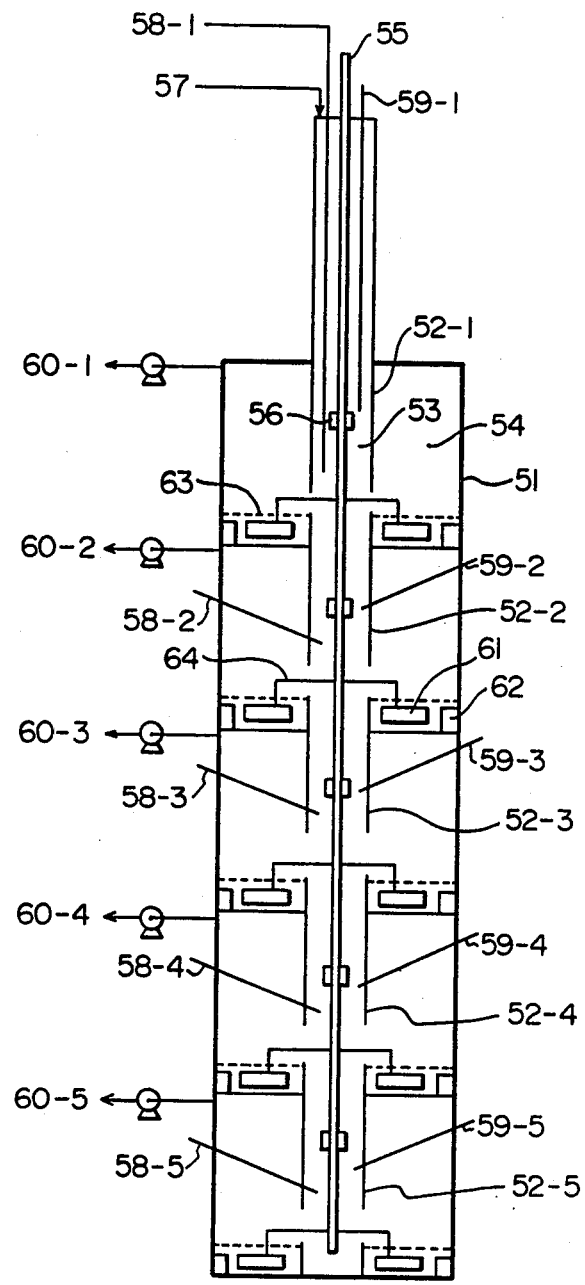
FIG. 15 is a simplified vertical sectional view of the multiunit culture apparatus of this invention for carrying out main culturing and settling of cells in a cell settling zone.

In FIG. 15, a culture apparatus 51 includes five culturing units.

Cylindrical partitions 52-1, 52-2, 52-3, 52-4 and 52-5 extend through the individual culturing units nearly centrally. In each of the culturing units, the cylindrical partition is cut at the bottom as shown in FIG. 15 so that a cell flowing zone 53 formed inwardly of the cylindrical partition communicates with a settling zone 54 formed exteriorly of the partition. A stirring rod 55 equipped with stirring impellers 56 is provided extending through the culturing units so as to stir the cell flowing zones of the individual units. Lines 58-1, 58-2, 58-3, 58-4, and 58-5 for supplying oxygen or an oxygen-containing gas are provided in the cell flowing zones of the units, and sensors 59-1, 59-2, 59-3, 59-4 and 59-5 are also provided for detecting the oxygen concentrations of the cell flowing zones.

A fresh culture medium is supplied to the apparatus from a supplying line 57, and the spent medium is withdrawn via lines 60-1, 60-2, 60-3, 60-4 and 60-5 of the individual units.

A liquid medium such as a perfluorocarbon is placed at the bottom of each of the culturing units to form a liquid medium layer. The dotted line 63 in FIG. 15 shows the interface between the liquid medium layer and the culture medium. A baffle late 62 is provided in each of the units so as to be positioned within the liquid medium. In each of the units, a stirring impeller 61 is fixed to a supporting rod 64 extending from the stirring rod 55 so as to stir the liquid medium.

When the stirring rod 55 is rotated, the stirring impeller stirs the culture medium within the cell flowing zone, and the liquid medium is also stirred by the stirring impeller 61. Turning of the stirred liquid medium is baffled by the baffle plate 62, and the surface of the liquid medium undulates. This undulation is transmitted to the culture medium within the settling zone over the liquid medium to maintain the cells within the culture medium in suspension.

The following examples illustrate the present invention more specifically.

EXAMPLE 1

(1) Culture tank

A glass vessel having an inner capacity of about 200 ml and the structure shown in FIG. 1 was used as a culture tank. The height (H)/diameter (D) ratio of the culture tank was 2:1. The culture tank had a settling zone, as shown in FIG. 1, to which the stirring effect did not substantially extend. The V/S in this zone was 5.3 [cm], and h was 8 cm.

(2) Culture medium

There was used a culture medium prepared by adding 9 microgams/ml of insulin, 10 micrograms/ml of transferrin, 10 micromoles/ml of ethanolamine, and $2 \times 10^{-8}$ mole/liter of selenious acid as proliferation factors (ITES representing the initials of these substances) to a basal medium composed of a 2:1:1 mixture of RPMI 1640 medium, HAM R-12 medium and Dulbecco's modified Eagle medium.

(3) Culture method

The culture medium was put in the culture tank so as to provide a liquid volume of 150 ml. IgG-producing mouse-mouse hybridoma cells 4C10B5 derived from mouse myeloma cells P3UI and mouse B cells were seeded at a density of $8.0 \times 10^5$ cells/ml.

Air containing 5% of carbon dioxide and oxygen containing 5% of carbon dioxide gas were supplied to the suspension in the culture tank. The supply of these gases was controlled such that the pH of the suspension was kept constant at 6.5 to 7.0 and the amount of oxygen dissolved therein was kept constant within the range of 3 to 4 ppm.

The suspension in the culture tank was maintained at 37.0° C., and a marine-type stirrer in the culture tank was rotated at a speed of 60 rpm.

Immediately after the initiation of the cultivation, supplying of the makeup culture medium and the discharging of the spent medium were started. The amount of the makeup culture medium supplied to the culture tank was 150 ml per day. Five days after the starting of the culture, the amount of the makeup culture medium supplied was increased to 300 ml per day.

(4) Results of culture

After culturing for 7 days, the results shown in Table 1 were obtained.

TABLE 1

| Culture period (days) | Cell density (cells/ml) |
|---|---|
| 1 | $8.0 \times 10^5$ |
| 2 | $7.5 \times 10^5$ |
| 3 | $1.0 \times 10^6$ |
| 4 | $1.2 \times 10^6$ |
| 5 | $2.9 \times 10^6$ |
| 6 | $4.5 \times 10^6$ |
| 7 | $6.4 \times 10^6$ |

COMPARATIVE EXAMPLE 1

The same culture tank and culture medium as used in Example 1 were used.

The culture medium was put in the culture tank so as to provide a liquid volume of 150 ml. 4C10B6 cells were seeded at a cell density of $8.0 \times 10^5$ cells/ml.

The cells were cultured under the same conditions as in Example 1 except that no makeup culture medium was supplied, and the spent medium was not discharged. The results obtained by performing the culture for 5 days are shown in Table 2.

TABLE 2

| Culture period (days) | Living cell density (cells/ml) |
|---|---|
| 1 | $8.0 \times 10^5$ |
| 2 | $7.5 \times 10^5$ |
| 3 | $1.5 \times 10^6$ |
| 4 | $1.2 \times 10^6$ |
| 5 | Died |

COMPARATIVE EXAMPLE 2

(1) Culture method

A 100 ml spinner flask made by Shibata Hario Glass Co., Ltd. was used as a culture tank.

The same culture medium as used in Example 1 was put in the flask so as to provide a liquid volume of 100 ml. Mouse-mouse hybridoma 4C10B6 cells derived from mouse myeloma P3U1 were seeded in the culture tank at a cell density of $8.0 \times 10^5$ cells/ml, and cultured under the same conditions as in Example 1.

After the starting of the culture, a makeup culture medium having the same composition as the medium initially added was supplied, and the spent medium was discharged, through lines attached to the flask. The amount of the makeup medium supplied was 100 ml per day.

(2) Results of culture

When the culture was carried out for 8 days, the results shown in Table 3 were obtained.

TABLE 3

| Culture period (days) | Cell density (cells/ml) |
| --- | --- |
| 1 | $8.0 \times 10^5$ |
| 2 | $6.3 \times 10^5$ |
| 3 | $5.0 \times 10^5$ |
| 4 | $3.9 \times 10^5$ |
| 5 | $3.1 \times 10^5$ |
| 6 | $2.4 \times 10^5$ |
| 7 | $1.9 \times 10^5$ |
| 8 | $1.5 \times 10^5$ |

EXAMPLE 2

(1) Results of culture

Figure 10:
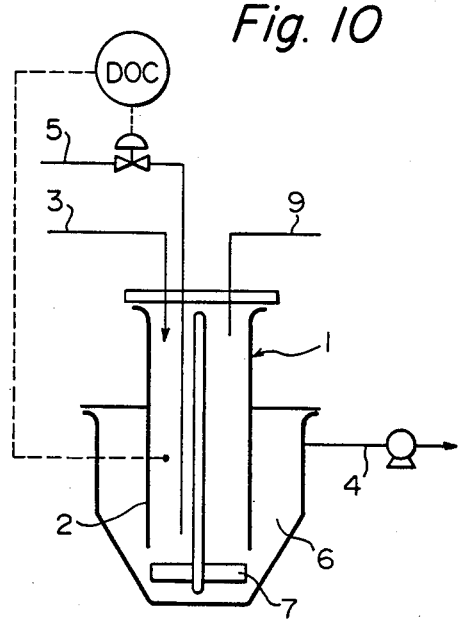
FIG. 10 is a simplified vertical sectional view of the apparatus of this invention used in Examples 2 to 13 given hereinbelow.

The culture system shown in FIG. 10 was used. The system comprised a culture tank 1 including a settling zone 6 separated by a partition wall 2 provided inwardly of the wall of the tank, a line 4 in the upper portion of the tank for discharging the culture liquid, and a marine-type stirrer 7 in the lower portion of the tank. The net culture volume of the tank was about 200 ml. V, D, d, and H were respectively 120 ml, 6.5 cm, 4.5 cm, and 14 cm.

(2) Culture medium

A 2:1:1 mixture of RPMI 1640 medium, HAM F12 medium and Dulbecco's modified Eagle medium with further addition of amino acids, glucose, etc. (to be referred to as eRDF) was used as a basal medium. To the basal medium was added 9 micrograms/ml of insulin, 10 micrograms/ml of transferrin, 10 micromoles/liter of ethanolamine and $2 \times 10^{-8}$ mole/liter of sodium selenite as growth factors to form a culture medium.

(3) Culture method

The culture tank was sterilized by autoclaving, and charged with the culture medium prepared in (2). Mouse-human hybridoma H1 cells (IgG-producing cells) derived from mouse myeloma P3U1 were seeded at a density of $2.5 \times 10^5$ cells/ml. Oxygen gas containing 5% of carbon dioxide gas was introduced into the culture tank through a blow nozzle 5 so that by automatic control, the concentration of dissolved oxygen was adjusted to 3 ppm. After contact with the culture medium, the gas was taken out of the system from a nozzle 9. The culture medium in the culture tank was maintained at 37° C. The stirrer was rotated at a speed of 35 rpm.

For one day after seeding, the culture was performed batchwise. Thereafter, perfusion culture was started. Specifically, a makeup culture medium having the same composition as above was introduced from a nozzle 3, and the spent medium from which the cells were separated was withdrawn from the system via a line 4. As a measure of perfusion, the ratio of the amount of the makeup culture medium supplied per day to the effective culture volume was determined.

(4) Results of culture

The results obtained after performing the culture for 13 days, were shown in Table 4.

EXAMPLE 3

(1) Culture apparatus

The same culture apparatus as used in Example 1 was used but incresed in scale. The V, D, d and H of this apparatus were 1200 ml, 13 cm, 8.5 cm, and 26.5 cm, respectively. Its V/S was about 15 cm.

(2) Culture medium

A culture medium prepared by adding insulin, transferrin, ethanolamine, sodium selenite and 0.5%(w/v) bovine serum albumin (BSA) to the basal medium eRDF was used.

(3) Culture method

Same as in Example 1.

(4) Results of culture

Shown in Table 5.

EXAMPLE 4

Example 2 was repeated except that the same culture medium as used in Example 3 was used. The results are shown in Table 6.

EXAMPLE 5

Example 2 was repeated except that a culture medium prepared by adding 10% (w/v) of fetal calf serum (FCS) to the basal medium eRDF was used. The results are shown in Table 7.

EXAMPLE 6

Example 2 was repeated except that from the 8th day of the culture and thereafter, 0.02% (w/v) of Pluronic F68 was added, and IgG-producing mouse-human hybridoma H2 cells derived from mouse myeloma P3U1 were cultured. The results are shown in Table 8.

EXAMPLE 7

Example 2 was repeated except that the same culture medium as in Example 3 was used and the same cells as in Example 6 were cultured. The results are shown in Table 9.

EXAMPLE 8

Example 2 was repeated except that a culture medium prepared by adding 0.5% (w/v) of human serum albumin (HSA) was added to ITES-eRDF was used, and the same cells as in Example 6 were used. The results are shown in Table 10.

EXAMPLE 9

Example 2 was repeated except that the same culture medium as in Example 5 was used and the same cells as in Example 6 were cultured. The results are shown in Table 11.

EXAMPLE 10

Example 2 was repeated except that the same culture medium as in Example 3 was used, and IgG-producing mouse-human hybridoma H3 cells derived from mouse myeloma P3U1 were cultured. The results are shown in Table 12.

EXAMPLE 11

Example 2 was repeated except that the same culture medium as in Example 3 was used, and IgG-producing mouse-human hybridoma V1 cells derived from mouse myeloma P3U1 cells were cultured. The results are shown in Table 13.

EXAMPLE 12

Example 2 was repeated except that the same culture medium as in Example 3 was used and on the 19th day of the culture and thereafter, 0.02% (w/v) of Pluronic F68 was added, and that IgG-producing mouse-human hybridoma V2 cells derived from mouse myeloma P3U1 cells were cultured. The results are shown in Table 14.

EXAMPLE 13

Example 2 was repeated except that the same culture medium as in Example 3 was used, and IgG-producing mouse-human hybridoma V6 cells derived from mouse myeloma P3U1 cells were cultured. The results are shown in Table 15.

EXAMPLE 14

(1) Culture tank

A culture tank consisting of four stacked culturing units each having a capacity of 350 ml, as shown in FIG. 11, was used. This culture tank includes a settling zone to which no stirring force extends. A stirring impeller 28 is provided in this tank so that by rotating the impeller, cells are maintained in suspension. The H:D ratio of the culture tank is about 6:1.

(2) Culture medium

As a basal medium, a 2:1:1 mixture of RPMI 1640 medium, HAM-F12 medium and Dulbecco's modified Eagle medium supplemented with amino acids, glucose, etc. was used (this basal medium will be referred to hereinafter as eRDF), and 9 $\mu$g/ml of insulin, 10 $\mu$g/ml of transferrin, 10 $\mu$M of ethanolamine and 20 nM of selenous acid (ITES) were added as proliferation factors.

(3) Culture method

About 1.4 liters of the culture medium was put in the culture tank. Mouse-human hybridoma C23 strain cells derived from mouse myeloma P3U1 as parent cells were seeded in the culture medium at a density of $5.6 \times 10^5$ cells/ml. The stirring impeller was rotated at a speed of about 40 rpm, and the cells were cultured. At this time, the cells existed in the tank as about 1 liter of a suspension.

These cells were capable of producing immunoglobulin (IgG). Air containing 5% of $CO_2$ and oxygen gas were supplied to the culture tank, and during the culture, the pH was maintained at 6.5 to 7.0, and the concentration of dissolved oxygen was adjusted to 3 to 4 ppm. Replacing the culture medium was started on the day on which the culture was started, and carried out at a flow rate of 0.5 liter/day to 2 liters/day. The culture tank was maintained at 37° C.

(4) Results of the culture

The results of the culture are shown in Table 16.

EXAMPLE 15

(1) Culture tank

A culture tank having a capacity of about 10 liters as shown in FIG. 14 was used. This tank included a settling zone to which no stirring force extends. About 1.2 liters of a fluorocarbon was placed at the bottom of the tank so as to submerge stirring impeller 38 and baffle plate 39 therein and adapted to be stirred. The H:D ratio in the culture tank of FIG. 14 was about 1:1.

(2) Culture medium

A 1:2:1 mixture of Dulbecco's modified Eagle medium, RPMI 1640 and HAM F 12 medium was mixed with various amino acids, glucose, sodium pyruvate, thymidine, choline chloride, inositol, etc. to prepare a basal medium. The basal medium was supplemented with insulin, transferrin, ethanolamine, selenite and FCS, and used in the culture.

(3) Culture method

About 8 liters of the culture medium was put in the culture tank shown in FIG. 14. Mouse-human hybridoma C23 strain cells derived from mouse myeloma P3U1 as parent cells were seeded in the culture medium. The stirring impeller was rotated at a speed of about 20 rpm, and the cells were cultured. At this time, the cells existed in the tank as about 4 liters of a suspension.

These cells were capable of producing immunoglobulin (IgG). Air containing 5% of $CO_2$ and oxygen gas were supplied to the culture tank, and during the culture, the pH was maintained at 6.5 to 7.0, and the concentration of dissolved oxygen was adjusted to 3 to 4 ppm. Replacing the culture medium was started on the day on which the culture was started, and carried out at a flow rate of 2 liters/day to 8 liters/day. The culture tank was maintained at 37° C.

(4) Results of the culture

The results of the culture are shown in Table 17.

EXAMPLE 16

(1) Culture tank

A stack of five culturing units each having a capacity of about 10 liters as shown in FIG. 15 was used as a culture tank. This tank had settling zones to which no stirring power extended as shown in FIG. 15. About 1.2 liters of a fluorocarbon was placed at the bottom of each unit to permit submerging of the stirring rod 11 and the baffle 1 and adapted to be stirred. The H:D ratio in the culture tank of FIG. 15 was 5:1.

(3) Culture method

Fifty liters of the culture medium was placed in a culture tank of the type shown in FIG. 15. Mouse-human hybridoma C23 strain cells derived from mouse myeloma P3U1 as parent cells were seeded at a density of $1.1 \times 10^5$ cells/ml. These cells were capable of producing immunoglobulin G (IgG). The cells were cultured by rotating the stirring impeller at a speed of about 20 rpm. At this time, the cells existed in the tank as about 20 liters of a suspension. Oxygen gas was blown into the culture medium from a nozzle and the concentration of dissolved oxygen gas adjusted to 3 to 4 ppm. Replacing the culture medium was started 3 days after the beginning of culturing, and carried out at a rate of 10 liters/day to 40 liters/day. The culture tank was maintained at 37° C.

(4) Results of the culture

The results of culturing are shown in Table 18.

TABLE 4

Cells: Mouse-human hybridoma H1
Medium: ITES-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.2 | — | — |
| 1 | 0 | 0.5 | — | — |
| 2 | 1 | 0.4 | — | — |
| 3 | 1 | 0.3 | — | — |
| 4 | 1 | 0.6 | 3.2 | 8.8 |
| 5 | 1 | 0.9 | — | — |
| 6 | 2 | 1.6 | 7.2 | 6.2 |
| 7 | 2 | 2.2 | — | — |
| 8 | 2.5 | 3.2 | 9.0 | 7.2 |
| 9 | 2.5 | 4.6 | — | — |
| 10 | 2.5 | 5.9 | 8.8 | 6.4 |
| 11 | 4 | 5.2 | — | — |
| 12 | 4 | 6.6 | — | — |
| 13 | 4 | 7.3 | 12 | 8.7 |

TABLE 5

Cells: Mouse-human hybridoma H1
Medium: ITES-0.5% BSA-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.2 | — | — |
| 1 | 0 | 0.2 | 1.4 | — |
| 2 | 0 | 0.3 | 3.1 | — |
| 3 | 1 | 0.4 | 3.7 | 8.0 |
| 4 | 1 | 0.5 | 3.9 | 6.7 |
| 5 | 1 | 0.5 | 4.2 | 7.0 |
| 6 | 1.5 | — | — | — |
| 7 | 1.5 | 1.0 | 6.0 | 7.8 |
| 8 | 1.5 | 1.2 | 11 | 12 |
| 9 | 1.5 | 1.6 | 11 | 9.0 |
| 10 | 1.5 | 2.0 | 14 | 9.3 |
| 11 | 2 | 2.7 | 14 | 8.3 |
| 12 | 2.5 | 3.8 | 12 | 7.8 |
| 13 | 2.5 | 4.6 | 9.4 | 6.6 |
| 14 | 4 | 5.0 | 8.4 | 6.5 |
| 15 | 4 | 7.0 | 8.8 | 5.0 |
| 16 | 4.5 | 8.5 | 8.8 | 4.7 |

TABLE 6

Cells: Mouse-human hybridoma H1
Medium: ITES-0.5% BSA-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.4 | — | — |
| 1 | 2 | 0.5 | 2.8 | 10 |
| 2 | 2 | 0.8 | — | — |
| 3 | 2 | 1.1 | 3.5 | 5.5 |
| 4 | 2 | 1.9 | — | — |
| 5 | 2 | 3.6 | 9.5 | 4.5 |
| 6 | 4 | 4.5 | — | — |

TABLE 6-continued

Cells: Mouse-human hybridoma H1
Medium: ITES-0.5% BSA-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 7 | 4 | 6.0 | 11 | 6.8 |
| 8 | 4.5 | 8.0 | — | — |
| 9 | 4.9 | 9.7 | 11 | 5.2 |

TABLE 7

Cells: Mouse-human hybridoma H1
Medium: 10% FCS-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.5 | — | — |
| 1 | 1.5 | 0.6 | 3 | 3 |
| 2 | 1.5 | 0.9 | — | — |
| 3 | 1.5 | 1.2 | 3 | 2 |
| 4 | 1.5 | 1.5 | — | — |
| 5 | 1.5 | 2.0 | — | — |
| 6 | 1.5 | 1.4 | 5 | 2.5 |
| 7 | 3.5 | 1.0 | — | — |
| 8 | 3.5 | 1.4 | — | — |
| 9 | 3.5 | 2.6 | 3 | 3 |
| 10 | 3.5 | 3.4 | — | — |
| 11 | 3.5 | 3.9 | — | — |
| 12 | 3.5 | 4.3 | 4 | 2.5 |
| 13 | 5 | 5.0 | — | — |
| 14 | 5 | 7.3 | — | — |
| 15 | 5 | 8.5 | — | — |
| 16 | 5 | 8.8 | 7 | 2.5 |
| 17 | 5 | 9.8 | — | — |

TABLE 8

Cells: Mouse-human hybridoma H2
Medium: ITES-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.7 | — | — |
| 1 | 0 | 0.8 | 7.7 | — |
| 2 | 2 | 0.6 | 10 | — |
| 3 | 2 | 1.3 | 11 | 16 |
| 4 | 4 | 2.0 | 8.7 | 16 |
| 5 | 4 | 3.0 | 13 | 15 |
| 6 | 5.5 | 4.1 | 24 | 22 |
| 7 | 7 | 6.8 | 22 | 18 |
| 8 | 7 | 6.8 | 23 | 23 |
| 9 | 7 | 8.0 | 30 | 26 |
| 10 | 7 | 11 | 30 | 20 |

TABLE 9

Cells: Mouse-human hybridoma H2
Medium: ITES-0.5% BSA-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.8 | — | — |
| 1 | 2 | 0.8 | 12 | — |
| 2 | 2 | 1.5 | 22 | 27 |
| 3 | 4 | 1.7 | 24 | 27 |
| 4 | 5.5 | 2.6 | 19 | 28 |
| 5 | 7 | 3.5 | 17 | 27 |
| 6 | 7 | 4.6 | 21 | 31 |

TABLE 9-continued

Cells: Mouse-human hybridoma H2
Medium: ITES-0.5% BSA-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 7 | 7 | 5.8 | 25 | 30 |
| 8 | 7 | 6.0 | 30 | 35 |
| 9 | 7 | 7.4 | 40 | 37 |
| 10 | 7 | 9.4 | 43 | 32 |
| 11 | 7 | 11 | 50 | 31 |
| 12 | 7 | 12 | 52 | 30 |

TABLE 10

Cells: Mouse-human hybridoma H2
Medium: ITES-0.5% HAS-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 1.2 | — | — |
| 1 | 2 | 1.5 | 10 | 13 |
| 2 | 4 | 2.5 | 17 | 13 |
| 3 | 4 | 4.0 | 19 | 19 |
| 4 | 7 | 5.5 | 35 | 25 |
| 5 | 7 | 7.4 | 30 | 28 |
| 6 | 7 | 8.6 | 30 | 24 |
| 7 | 7 | 8.1 | 29 | 24 |
| 8 | 7 | 10 | 51 | 33 |
| 9 | 7 | 11 | 46 | 29 |

TABLE 11

Cells: Mouse-human hybridoma H2
Medium: 10% FCS-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.6 | — | — |
| 1 | 2 | 0.6 | 7.6 | — |
| 2 | 2 | 1.5 | 7.0 | 7.8 |
| 3 | 3.5 | 2.6 | 28 | 18 |
| 4 | 3.5 | 3.8 | 36 | 34 |
| 5 | 5 | 6.2 | 50 | 28 |
| 6 | 5 | 9.0 | 50 | 28 |
| 7 | 7 | 13 | 70 | 27 |
| 8 | 7 | 16 | 69 | 30 |
| 9 | 7 | 21 | 50 | 16 |

TABLE 12

Cells: Mouse-human hybridoma H3
Medium: ITES-0.5% BSA-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.4 | — | — |
| 1 | 0 | 0.4 | — | — |
| 2 | 2 | 0.7 | 10 | 15 |
| 3 | 2 | 0.5 | — | — |
| 4 | 2 | 0.7 | 12 | 18 |
| 5 | 2 | 0.8 | — | — |
| 6 | 2 | 0.8 | 18 | 20 |
| 7 | 2 | 1.3 | — | — |
| 8 | 2 | — | — | — |
| 9 | 2 | 1.7 | 20 | 16 |
| 10 | 2 | 2.0 | — | — |
| 11 | 2 | 2.3 | 30 | 10 |
| 12 | 2 | 2.4 | — | — |

TABLE 12-continued

Cells: Mouse-human hybridoma H3
Medium: ITES-0.5% BSA-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 13 | 3.5 | 3.1 | 34 | 15 |
| 14 | 3.5 | 3.5 | — | — |
| 15 | 3.5 | — | — | — |
| 16 | 3.5 | 4.1 | 20 | 10 |
| 17 | 3.5 | — | — | — |
| 18 | 3.5 | 5.0 | 23 | 10 |
| 19 | 3.5 | 0 | — | — |
| 20 | 3.5 | 6.3 | 41 | 14 |
| 21 | 4.5 | — | — | — |
| 22 | 4.5 | 10 | — | — |

TABLE 13

Cells: Mouse-human hybridoma V1
Medium: ITES-0.5% BSA-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.1 | — | — |
| 1 | 2 | 0.1 | — | — |
| 2 | 2 | 0.2 | 3.9 | 35 |
| 3 | 2 | 0.5 | 4.6 | 19 |
| 4 | 2 | 0.9 | 6.0 | 15 |
| 5 | 2 | 0.9 | — | — |
| 6 | 2 | 1.2 | 11 | 21 |
| 7 | 3.5 | 1.2 | — | — |
| 8 | 5 | 1.7 | 15 | 32 |
| 9 | 7 | 2.7 | 13 | 25 |
| 10 | 7 | 3.8 | 12 | 23 |
| 11 | 7 | 4.8 | 13 | 20 |
| 12 | 7 | 4.9 | — | — |
| 13 | 7 | 5.1 | 13 | 18 |

TABLE 14

Cells: Mouse-human hybridoma V2
Medium: ITES-0.5% BSA-eRDF

| Culturing time (days) | Amount of the makeup medium as a multiple of the net culture volume | Cell density ($\times 10^6$ cells per ml) | Antibody concentration ($\mu g/ml$) | Antibody (IgG) producing speed ($\mu g/10^6$ cells · day) |
|---|---|---|---|---|
| 0 | 0 | 0.3 | — | — |
| 1 | 0 | 0.4 | — | — |
| 2 | 2 | 0.7 | 16 | — |
| 3 | 2 | 0.9 | 16 | 35 |
| 4 | 2 | 1.1 | 17 | 31 |
| 5 | 2 | 1.2 | — | — |
| 6 | 2 | 1.6 | 22 | 28 |
| 7 | 4 | 2.0 | 32 | 31 |
| 8 | 4 | 2.8 | 21 | 30 |
| 9 | 4 | 3.3 | — | — |
| 10 | 4 | 4.2 | 31 | 30 |
| 18 | 8 | 4.7 | 22 | 36 |
| 19 | 8 | 4.3 | 21 | 38 |
| 20 | 8 | 4.2 | 22 | 40 |
| 21 | 8 | 5.4 | 27 | 38 |
| 22 | 8 | 6.5 | 24 | 29 |
| 23 | 8 | 6.6 | 39 | 45 |
| 24 | 8 | 6.8 | 4.7 | 54 |

TABLE 15

Cells: Mouse-human hybridoma V6
Medium: ITES-0.5% BSA-eRDF

| Culturing time (days) | Amount of the makeup medium as a multiple of the net culture volume | Cell density (× $10^6$ cells per ml) | Antibody concentration (μg/ml) | Antibody (IgG) producing speed (μg/$10^6$ cells · day) |
|---|---|---|---|---|
| 0 | 0 | 1.1 | — | — |
| 1 | 0 | — | — | — |
| 2 | 2 | 1.6 | 4.4 | — |
| 3 | 4 | 1.6 | 4.3 | 5.5 |
| 4 | 4 | 1.9 | 3.5 | 7.0 |
| 5 | 4 | 2.2 | 2.7 | 4.9 |
| 6 | 4 | 3.4 | 4.2 | 4.9 |
| 7 | 4 | 4.2 | 4.4 | 4.2 |
| 8 | 4 | 3.7 | 3.9 | 4.2 |
| 9 | 5.5 | 4.1 | 3.2 | 4.3 |
| 10 | 5.5 | 4.0 | 4.4 | 6.0 |
| 11 | 5.5 | 5.5 | 5.0 | 5.0 |
| 12 | 5.5 | 6.7 | 9.0 | 7.4 |
| 13 | 8 | 10 | 9.0 | 5.0 |
| 14 | 8 | 13 | 9.0 | 5.6 |

TABLE 16

| Culture period (days) | Cell density (cells/ml) | Amount of the culture medium replaced (liters/day) |
|---|---|---|
| 1 | $5.6 \times 10^5$ | 0.5 |
| 2 | $1.2 \times 10^5$ | 1.0 |
| 3 | $2.5 \times 10^6$ | 1.0 |
| 4 | $5.2 \times 10^6$ | 2.0 |
| 5 | $9.8 \times 10^6$ | 2.0 |
| 6 | $1.1 \times 10^7$ | 2.0 |

TABLE 17

| Culture period (days) | Cell density (cells/ml) | Amount of the culture medium replaced (liters/day) |
|---|---|---|
| 0 | $7.1 \times 10^5$ | 2 |
| 1 | $1.7 \times 10^6$ | 4 |
| 2 | $4.1 \times 10^6$ | 4 |
| 3 | $5.8 \times 10^6$ | 8 |
| 4 | $6.7 \times 10^6$ | 8 |
| 5 | $1.0 \times 10^7$ | 8 |

TABLE 18

| Culture period (days) | Cell density (cells/ml) | Amount of the culture medium replaced (liters/day) |
|---|---|---|
| 1 | $1.1 \times 10^5$ | — |
| 2 | $2.1 \times 10^5$ | — |
| 3 | $4.0 \times 10^5$ | 10 |
| 4 | $7.6 \times 10^5$ | 10 |
| 5 | $1.3 \times 10^6$ | 20 |
| 6 | $2.5 \times 10^6$ | 20 |
| 7 | $4.8 \times 10^6$ | 20 |
| 8 | $8.7 \times 10^6$ | 40 |
| 9 | $9.9 \times 10^7$ | 40 |
| 10 | $1.1 \times 10^7$ | 40 |

What we claim is:

1. An apparatus for cell culture by perfusion comprising a cell culture tank for suspension culture, said cell culture tank having a suspension cell culture zone, a cell settling zone, an opening for discharging a spent culture medium from the settling zone and an opening for supplying a culture medium to the suspension culture zone, the suspension culture zone and the settling zone being separated by a partition therebetween in a manner to communicate with each other in the lower portion of the settling zone, and the settling zone being formed between the side wall of the cell culture tank and the partition.

2. The apparatus of claim 1 wherein the settling zone is formed between the side wall of the cell culture tank and the partition in a manner to surround the suspension culture zone.

3. The apparatus of claim 1 wherein the settling zone has means for facilitating the settling of the cells.

4. The apparatus of claim 1 wherein the suspension culture zone is separated from the settling zone by a cylindrical partition.

5. The apparatus of claim 1 wherein the suspension culture zone is separated from the settling zone by a cylindrical partitiion, a substantial portion of the side wall of the tank facing the cylindrical support is cylindrical, and wherein the cylindrical partition and the cylindrical portion of the side wall of the tank are positioned substantially concentrically.

6. The apparatus of claim 1 which further includes mechanical stirring means for forcibly suspending the cells in the culture medium.

7. The apparatus of claim 1 which further includes an oxygen-containing gas introduction opening and an oxygen-containing gas guiding cylinder whereby the cells in the culture medium are forcibly suspended under the effect of stirring created by the rising of the oxygen-containing gas through the guiding cylinder.

8. A method for culturing cells by perfusion in the culture apparatus of claim 1 which comprises withdrawing a substantially cell-free culture medium from the settling zone and introducing a fresh culture medium into the suspension culture zone.

9. The method of claim 9 wherein the ratio of the volume (V, cm$^3$) of the culture medium within the suspension cell culture zone to the effective settling zone (S, cm$^2$), V/S, is within the range of 0.1 to 500 cm.

10. A multiunit cell culture apparatus for cell suspension, comprising at least two culturing units and an opening for supplying a culture medium, each of said units comprising a culture zone for suspension culture of cells, a cell settling zone and a discharge opening for the culture medium from the top of the settling zone, said suspension culture zone and said settling zone being separated from each other by a partition so that they communicate with each other through the bottom part of the settling zone, said settling zone being formed between the outside wall of the culturing unit and the partition, and the culturing units being stacked longitudinally so as to permit flowing of the culture medium.

11. The method of claim 10 wherein the cells are animal cells.

12. A cell culture apparatus for perfusion culture comprising a cell culture tank for suspension culture, said cell culture tank having a molecular oxygen supply zone, a cell settling zone, a discharge opening for discharging the culture medium from the settling zone and a culture medium supply opening, the molecular oxygen supply zone and the settling zone being separated from each other by a partition so as to communicate with each other through the bottom of the settling zone, the settling zone being formed between the partition and the side wall of the cell culture tank, and the main culturing and settling of cells being carried out in the cell settling zone.

13. A cell culture apparatus for suspension culture comprising at least two culturing units and an opening for supply of a culture medium, each of the units comprising a cell flowing zone, a cell settling zone and a discharge opening for discharge of the culture medium from the top of the settling zone, the cell flowing zone and the cell settling zone in each said unit being separated from each other by a partition so as to communicate with each other through the bottom of the settling zone, said settling zone being formed between the outside wall of the culturing unit and the partition, the culturing units being stacked longitudinally so as to permit flowing of the culture medium through the flowing zone, the main culturing and settling in each unit being carried out in the cell settling zone.

14. A method of culturing cells by perfusion using a cell culture apparatus for perfusion culture comprising a cell culture tank for suspension culture, said cell culture tank having a molecular oxygen supply zone, a cell settling zone, a discharge opening for discharging the culture medium from the settling zone and a culture medium supply opening, the molecular oxygen supply zone and the settling zone being separated from each other by a partition so as to communicate with each other through the bottom of the settling zone, the settling zone being formed between the partition and the side wall of the cell culture tank, said method comprising forming at the bottom of the culture tank of the above culture apparatus a layer of a liquid medium which (a) is not substantially miscible with water, (b) has a higher density than water, and (c) does not substantially inhibit the growth of animal cells, culturing the animal cells while stirring the layer of the liquid medium and transmitting the effect of this stirring to the culture medium located on the liquid medium, withdrawing the culture medium substantially free from the cells from the settling zone, and introducing a fresh culture medium into the culture tank.

15. The method of claim 14 wherein the upper surface of the liquid medium layer does not reach the bottom of the partition.

* * * * *